United States Patent [19]

Zimmermann et al.

[11] Patent Number: 5,378,350

[45] Date of Patent: Jan. 3, 1995

[54] PROCESS AND CATALYST FOR DEHYDROGENATION OR DEHYDROCYCLIZATION OF HYDROCARBONS

[75] Inventors: Heinz Zimmermann, Munich, Germany; Frederik Versluis, Amersfoort, Netherlands

[73] Assignee: Linde Aktiengesellschaft, Wiesbaden, Germany

[21] Appl. No.: 741,446

[22] PCT Filed: Dec. 12, 1989

[86] PCT No.: PCT/EP89/01517

§ 371 Date: Aug. 9, 1991

§ 102(e) Date: Aug. 9, 1991

[87] PCT Pub. No.: WO90/06907

PCT Pub. Date: Jun. 28, 1990

[30] Foreign Application Priority Data

Dec. 12, 1988 [DE] Germany .................. 3841800

[51] Int. Cl.⁶ .............. C10G 35/06; B01J 23/00; C07C 5/333; C07C 5/41
[52] U.S. Cl. ...................... 208/136; 208/64; 502/308; 502/317; 502/320; 502/344; 502/349; 585/631; 585/663; 585/418
[58] Field of Search ............ 208/136, 64; 502/320, 502/308, 317, 344, 349; 585/631, 663, 418

[56] References Cited

U.S. PATENT DOCUMENTS

| | | | |
|---|---|---|---|
| 2,249,337 | 7/1941 | Visser et al. | 208/136 |
| 2,311,979 | 2/1943 | Corson et al. | 208/136 |
| 2,371,087 | 3/1945 | Webb et al. | 208/136 |
| 2,374,404 | 4/1945 | Ahlberg | 585/433 |
| 2,380,035 | 7/1945 | Edson et al. | 585/418 |
| 2,437,532 | 3/1948 | Huffman | 208/136 |
| 2,668,142 | 2/1954 | Strecker et al. | 208/136 |
| 3,114,697 | 12/1963 | Bourne et al. | 208/136 |
| 4,151,071 | 4/1979 | Myers | 208/136 |
| 4,347,123 | 8/1982 | Mauldin et al. | 208/136 |
| 4,788,364 | 11/1988 | Harandi | 585/312 |

FOREIGN PATENT DOCUMENTS

| | | | |
|---|---|---|---|
| 620993 | 5/1961 | Canada | 208/136 |
| 2270938 | 1/1976 | France . | |
| 767855 | 3/1954 | Germany . | |
| 483417 | 5/1938 | United Kingdom . | |

*Primary Examiner*—Helen M. S. Sneed
*Assistant Examiner*—Walter D. Griffin
*Attorney, Agent, or Firm*—Millen, White, Zelano & Branigan

[57] ABSTRACT

Process and catalyst for dehydrogenation or dehydrocyclization of hydrocarbons. The catalyst consists of an aluminum oxide/chromium oxide support with promotors consisting of compounds of alkali metals and/or alkaline earth metals and compounds of metals from the third and/or fourth subgroups of the periodic table. Coke formation and side reactions can be substantially suppressed by the use of these catalysts under special operating conditions and special reactors.

18 Claims, 1 Drawing Sheet

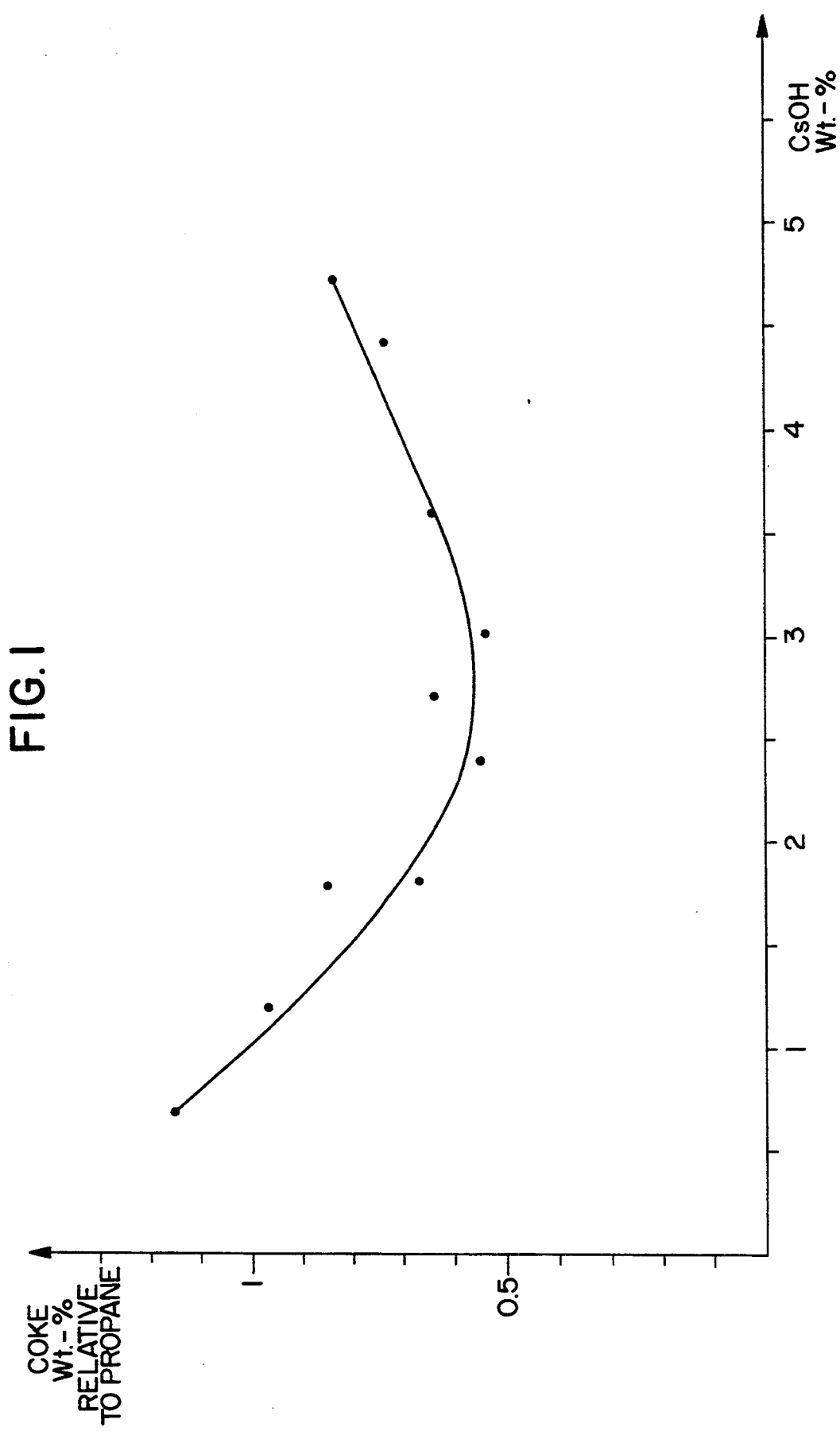

PROCESS AND CATALYST FOR DEHYDROGENATION OR DEHYDROCYCLIZATION OF HYDROCARBONS

BACKGROUND OF THE INVENTION

The invention relates to a process and a catalyst for dehydrogenation or dehydrocyclization of hydrocarbons on regenerable catalysts, consisting of chromium oxide and aluminum oxide with one or more promoters from the group of alkali metal and/or alkaline earth metal compounds and with at least one additional promoter.

It is generally known that hydrocarbons can be dehydrogenated in the presence of suitable catalysts at higher temperature. Depending on the type of hydrocarbons used, in the case of paraffins especially as a function of the chain length, either a dehydrogenation to monoolefins or diolefins or, possibly also simultaneously, a cyclization i.e. ring formation, mainly to aromatic compounds, with simultaneous cleavage of hydrogen, a so-called dehydrocyclization, takes place.

Below, by the term "dehydrogenation" are understood all reactions in which hydrogen is cleaved from hydrocarbons of any type, without regard to whether the dehydrogenation products form straight or branched chains whether they are cyclic or whether they are singly or repeatedly unsaturated.

As can be seen, for example, from U.S. Pat. No. 3,719,721, aluminum oxide-chromium oxide catalysts are used for such dehydrogenation processes.

But since catalysts with aluminum oxide as support material exhibit acid properties, which lead to undesirable isomerization or cracking reactions, these known catalysts in addition contain a small portion of an alkali metal oxide and/or alkaline earth metal oxide, which acts as a base and thus improves the selectivity of the catalyst.

As other promoters, the known catalysts contain niobium or tantalum oxide or also, as a comparison example, cerium oxide, which contributes to increasing the catalyst activity.

Despite the improved selectivity and activity of the chromium oxide catalysts, in the dehydrogenation according to the process of the above-mentioned U.S. Patent, carbon or coke results, which is precipitated on the catalyst and deactivates it continuously, which means a considerable drawback relative to economy and investment costs.

The known process further has the drawback that the selectivity or activity of the catalyst is not sufficient to keep the by-product formation values optimally low—especially to prevent multiple dehydrogenations—to obtain pure monoolefin dehydrogenation products in a suitable feedstock stream.

SUMMARY OF THE INVENTION

Therefore, it is the object of this invention to configure a process and a catalyst of the above-mentioned type so that a minimal coke formation is achieved with simultaneous optimization of the investment and operating costs.

This object is achieved according to the invention in that the dehydrogenation or dehydrocyclization is performed on a catalyst, which, in addition to at least one alkali and/or alkaline earth promoter, comprises at least one metal compound of the elements of the third and/or fourth subgroups of the periodic table (excluding the elements with atomic numbers 58 to 71) as an additional promoter.

The catalyst according to the invention is distinguished by the characteristic feature that, despite its increased activity, coke formation and side reactions—such as, for example, multiple dehydrogenations, which, for example in the case of propane dehydrogenation, result in an undesirable formation of propadiene—are reduced to a minimum.

DESCRIPTION OF THE INVENTION

As suitable promoters from the group of alkali or alkaline earth compounds for the process of the invention there can be mentioned sodium, potassium, calcium or barium compounds. However, the results that can be achieved with cesium compounds as promoters are outstanding. Catalysts which contain 0.1 to 10, preferably 1 to 5, % by weight of a cesium compound, calculated as $Cs_2O$, have proven to be especially effective.

But catalysts according to the invention which as additional promoter contain a scandium, yttrium or lanthanum compound or a titanium, zirconium or hafnium compound, individually or in combination, have proven to be especially suitable. Zirconium compounds have proven to be very especially effective, in particular, if the zirconium compound, calculated as $ZrO_2$, constitutes 0.1 to 15, preferably 0.1 to 5 or 0.5 to 1.5, % by weight of the catalyst.

According to another design of the inventive idea, a catalyst comprises an $Al_2O_3$ support with 10 to 50, preferably 20 to 30, % by weight of chromium oxide, calculated as $Cr_2O_3$, relative to the total weight of the catalyst.

With such a catalyst according to the invention, a minimal coke formation with simultaneously high activity of the catalysts can be attained in combination with the selection of suitable promoters and their use in optimal concentration.

Especially the metal oxides of the elements of the fourth subgroup of the periodic table, such as the preferably used $ZrO_2$, act as thermal stabilizers and increase the activity of the catalysts.

The catalysts according to the invention can be used in diluted or undiluted state for the dehydrogenation. The latter has the advantage of a smaller volume for the reactors and thus smaller investment costs.

Because of the great endothermy of dehydrogenation reactions, as isothermal a performance of the reaction as possible is advisable at low reaction temperatures between 400 and 700° C. Especially suitable for this purpose are, for example, reactors of the "steam reformer type" with direct heating by ceiling burners.

It has proven to be especially advantageous to perform the dehydrogenation process according to the invention cyclically and to regenerate the catalysts used in suitable time intervals. In this way, it has been shown to be advantageous to keep the temperature over the length of the reactor basically at the same level, i.e., to operate isothermally, but in this case to permit it to increase slowly in the course of a cycle, to offset the catalyst activity decreasing in the course of a cycle.

Pressures between 1 and 5 bars have proven suitable as working pressures for the dehydrogenation.

Further, it has been shown here that a dependence of the coke formation on throughput exists, so that the dehydrogenation is performed advantageously with an hourly space velocity (GHSV) of 100 to 2000 normal liters of hydrocarbon per liter of catalyst per hour.

The raw materials usable in the process according to the invention depend on the desired product. Thus, $C_3$, $C_4$ or $C_5$ hydrocarbon cuts or their mixtures are used for the production of monoolefins, while $C_6$ to $C_{10}$ hydrocarbon cuts are used for the production of BTX aromatic compounds ("BTX"=benzene, toluene, xylene).

The process according to the invention, especially with said isothermal mode of operation, in combination with the catalysts according to the invention, yields, for example, in the production of monoolefins, a product so pure that it can be fed directly to a polymerization process, without the selective hydrogenation considered to be necessary in the known processes having to be interposed before the polymerization.

The catalysts according to the invention can be regenerated extraordinarily inexpensively in suitable time intervals and can again be restored to their full activity. The regeneration in this case is achieved by passage of air, which has a low content of oxygen relative to the atmospheric air. Oxygen contents between 2 and 20% by volume have proven suitable. The intervals, in which the catalysts according to the invention have to be regenerated, depend on the type of dehydrogenation process and the desired end products, but in general, intervals of 1 to 50, preferably 3 to 7, hours have proven practicable.

The production of the catalyst according to the invention can be performed in a way known in the art. In general, the catalyst according to the invention is obtained by application of chromium oxide and promoters to the support material produced separately. But it is equally possible to produce the aluminum oxide, laden with chromium oxide, in one step, i.e., before the precipitation of the promoters or simultaneously with it.

The basic component of the catalyst is the $Al_2O_3$ support, on which the chromium oxide is applied. The support material can have any configuration known from the catalytic technology. It can, e.g., be present as powder or also formed in the shape of rings, tablets, etc. and extrudates. The application of chromium oxide to the support material can take place in a way known in the art, e.g., by simultaneous precipitation of the aluminum oxide and of the chromium oxide from an aqueous solution containing aluminum and chromium ions. On the other hand, the catalyst precursor material (precursor) can also be produced from $Al_2O_3$, to which the chromium compounds are applied by using an impregnation or precipitation technique.

To apply the promoters to the catalyst precursor material, known precipitating techniques can be used. It is possible, e.g., to suspend the support material in a solution, which contains the components of the promoter precursor, which is followed by a precipitation of the metal compound or compounds. A usable description of a method, which makes use of this technique, is found in U.S. Pat. No. 4,113,658.

According to a preferred embodiment, the metal ions forming the promoters are applied to the support, which can already contain chromium oxide, by the support being impregnated with a solution of one or all promoters and optionally chromic salt, and the solution can contain metal ions in complex form, which is followed by a heat treatment, which is used to remove the water from the solution, and, if necessary, to convert the metal compound to the necessary active form. The amount of the solution used to impregnate the support material is preferably just large enough to fill the pore volume of the support material with the solution. But no excess liquid should be present ("incipient wetness" method).

According to another preferred embodiment, the catalyst according to the invention is produced in several stages. Namely the support material comprising $Al_2O_3$ is first impregnated with an aqueous solution of a salt of the first promoter and chromium salt according to the "incipient wetness" method. Then, the impregnated material is subjected to a heat treatment, in which the material is dried and calcined. Finally, the calcined material is impregnated with an aqueous solution of the other promoter (or other promoters). This material impregnated twice in this way is subsequently preferably dried but is subjected to no additional calcination step. Surprisingly, it was determined that the activity or selectivity of a catalyst calcined only once is better than the activity or selectivity of a catalyst calcined twice.

The production of various catalysts, usable according to the invention, is described briefly below.

In all examples, the composition of the catalyst is indicated with respect to the individual components in the form of the (hydr-)oxides. But this does not necessarily mean that all metal ions are present in the form of a compound, which corresponds to the specified chemical formula of the (hydr-)oxide. Thus, e.g., chromium can be present in the catalyst both as $Cr_2O_3$ and $CrO_3$.

BRIEF DESCRIPTION OF THE DRAWING

FIG. 1 is a graph of the percentage of coke deposit relative to the propane used vs. the percentage weight of CsOH in the catalyst.

EXAMPLE 1

The catalyst support was made of aluminum oxide in all cases. Such a support is designated Harshaw Al 3982 T⅛" in the trade.

Catalyst 1 was produced by using this support in the form of 1200 g of the tablets according to the "incipient wetness" method with a solution, which contained 532.8 g of $CrO_3$ and 28.0 g of zirconium oxyacetate (corresponding to 52% by weight of $ZrO_2$). After the impregnation, the product was dried for 3 hours at 140° C. in a vacuum and for 16 hours at 110° C. in air and calcined for 2 hours in air at 740° C. Then, an impregnation of the catalyst with potassium acetate and a two-stage drying, first for 3 hours at 140° C. in a vacuum and then for 16 hours at 110° C. in air, took place. Then, the product was calcined for 2 hours in air at 740° C.

This finally yielded a catalyst composition of 72.1% by weight of $Al_2O_3$, 25% by weight of $Cr_2O_3$, 0.9% by weight of $ZrO_2$ and 2% by weight of $K_{2O}$.

EXAMPLE 2

Production analogously to catalyst I, but impregnation with an NaOH solution.

Composition of catalyst II:

72.1% by weight of $Al_2O_3$, 25% by weight of $Cr_2O_3$, 0.9% by weight of $ZrO_2$ and 2% by weight of $Na_2O$.

EXAMPLE 3

Production analogously to catalyst I, but impregnation with an $NaNO_3$ solution.

Composition of Catalyst III 72.1% by weight of $Al_2O_3$, 25% by weight of $Cr_2O_3$, 0.9% by weight of $ZrO_2$ and 2% by weight of $Na_2O$.

EXAMPLE 4

Production analogously to catalyst I, but impregnation with a Ba(NO$_2$)$_2$ solution.

Composition of Catalyst IV 72.1% by weight of Al$_2$O$_3$, 25% by weight of Cr$_2$O$_3$, 0.9% by weight of ZrO$_2$ and 2% by weight of BaO.

EXAMPLE 5

Production analogously to catalyst I, but impregnation with a Ca(NO$_3$)$_2$ solution.

Composition of Catalyst V 73.1% by weight of Al$_2$O$_3$, 25% by weight of Cr$_2$O$_3$, 0.9% by weight of ZrO$_2$ and 1% by weight of CaO.

EXAMPLE 6

Catalyst VI was produced in the same way as catalyst I, but impregnated after the calcination with an NaOH solution. Then, the product was dried first for 3 hours in a vacuum at 100° C. and then for 16 hours in air at 100° C. It was essential that catalyst VI not be calcined once more after the drying.

Composition of Catalyst VI 72.2% by weight of Al$_2$O$_3$, 25% by weight of Cr$_2$O$_3$, 0.9% by weight of ZrO$_2$ and 2% by weight of NaOH.

EXAMPLE 7

Production analogously to catalyst VI, but impregnation with a CsOH solution.

Composition of Catalyst VII 72.3% by weight of Al$_2$O$_3$, 25% by weight of Cr$_2$O$_3$, 0.9% by weight of ZrO$_2$ and 1.8% by weight of CsOH.

EXAMPLE 8

Production analogously to catalyst VI, but impregnation with a CsOH solution.

Composition of Catalyst VIII 71.4% by weight of Al$_2$O$_3$, 25% by weight of Cr$_2$O$_3$, 0.9% by weight of ZrO$_2$ and 2.7% by weight of CsOH.

EXAMPLES 9 to 16

Catalysts IX to XVI were produced in the same way as catalyst VI, only with the difference that catalysts IX to XVI were impregnated with a solution of CrO$_3$ and zirconium acetate instead of with a solution of CrO$_3$ and zirconium oxyacetate. Further, catalysts IX to XVI differed in their CsOH contents.

Thus, the catalysts had the following composition:

Cat. IX 71.7% by weight of Al$_2$O$_3$, 25.0% by weight of Cr$_2$O$_3$, 0.9% by weight of ZrO$_2$, 2.4% by weight of CsOH, Cat. X 73.4% by weight of Al$_2$O$_3$, 25.0% by weight of Cr$_2$O$_3$, 0.9% by weight of ZrO$_2$, 0.7% by weight of CsOH, Cat. XI 72.9% by weight of Al$_2$O$_3$, 25.0% by weight of Cr$_2$O$_3$, 0.9% by weight of ZrO$_2$, 1.2% by weight of CsOH, Cat. XII 72.3% by weight of Al$_2$O$_3$, 25.0% by weight of Cr$_2$O$_3$, 0.9% by weight of ZrO$_2$, 1.8% by weight of CsOH, 25.0% by weight of Cr$_2$O$_3$, Cat. XIII 71.1% by weight of Al$_2$O$_3$, 0.9% by weight of ZrO2, 3.0% by weight of CsOH, Cat. XIV 70.5% by weight of Al$_2$O$_3$, 25.0% by weight of Cr$_2$O$_3$, 0.9% by weight of ZrO$_{2, 3.6}$% by weight of CsOH, Cat. XV 69.7% by weight of Al$_2$O$_3$, 25.0% by weight of Cr$_2$O$_3$, 0.9% by weight of ZrO$_2$, 4.4% by weight of CsOH, Cat. XVI 69.4% by weight of Al$_2$O$_3$, 25.0% by weight of Cr$_2$O$_3$, 0.9% by weight of ZrO$_2$, 4.7% by weight of CsOH.

All data in % by weight relates in this case to the total weight of the catalyst.

The catalysts were analyzed with respect to the coke formation occurring during a dehydrogenation on their surface, which is an important criterion for the catalyst activity during prolonged operating periods. For this purpose, laboratory tests were performed with propane as the hydrocarbon to be dehydrogenated. In this case, the dehydrogenating cycles were 6 hours each, and a tube reactor was used, with which almost isothermal reaction conditions were adjusted to a GHSV of 850 Nl/1/hr and a conversion of 30%.

The test results are represented in table 1, namely together with the various promoters according to the invention.

TABLE I

| Catalyst No. | 1st Promoter % by weight | Other Promoter % by weight | Carbon % by weight, relative to the use |
| --- | --- | --- | --- |
| I | 2 K$_2$O | 0.9 ZrO$_2$ | 1.660 |
| II | 2 Na$_2$O | 0.9 ZrO$_2$ | 1.126 |
| III | 2 Na$_2$O | 0.9 ZrO$_2$ | 1.200 |
| IV | 2 BaO | 0.9 ZrO$_2$ | 1.393 |
| V | 1 CaO | 0.9 ZrO$_2$ | 1.126 |
| VI | 2 NaOH | 0.9 ZrO$_2$ | 0.948 |
| VII | 1.8 CsOH | 0.9 ZrO$_2$ | 0.677 |
| VIII | 2.7 CsOH | 0.9 ZrO$_2$ | 0.653 |
| IX | 2.4 CsOH | 0.9 ZrO$_2$ | 0.559 |
| X | 0.7 CsOH | 0.9 ZrO$_2$ | 1.157 |
| XI | 1.2 CsOH | 0.9 ZrO$_2$ | 0.981 |
| XII | 1.8 CsOH | 0.9 ZrO$_2$ | 0.862 |
| XIII | 3.0 CsOH | 0.9 ZrO$_2$ | 0.556 |
| XIV | 3.6 CsOH | 0.9 ZrO$_2$ | 0.660 |
| XV | 4.4 CsOH | 0.9 ZrO$_2$ | 0.748 |
| XVI | 4.7 CsOH | 0.9 ZrO$_2$ | 0.855 |

It is clear that the action of the basic promoters with respect to the coke formation also depends on whether the catalyst is calcined once more or not after the impregnation with the alkali or alkaline earth solution (cf. catalysts I to V with VI to XVI).

Further, it can be seen from table I that cesium compounds, in comparison with the other alkalis and alkaline earths, prevent the coke formation most effectively. But this effect is dependent in a certain way on the concentration of the cesium compound in the catalyst.

In FIG. 1, the percentage coke deposit, relative to the propane used, is applied against the concentration of CsOH in the catalyst. As can be seen, there is a pronounced minimum of the coke formation between 2 and 3% by weight of CsOH. In these tests performed with propane, except for the very small coke formation, an extraordinarily high selectivity was achieved (selectivity=desired dehydrogenation product×100: hydrocarbon feedstock). The propylene product contained less than 5 ppm of propadiene. Thus it is also possible to feed the product resulting in the dehydrogenation, without interpolation of a selective hydrogenation, directly to a polypropylene extraction unit, with which a further advantage results in comparison with the known dehydrogenation processes, which make a downstream selective hydrogenation necessary.

Altogether, the process according to the invention thus makes it possible, in a simple and economical way with simultaneous minimal coke accumulation, to dehydrogenate or to dehydrocyclize hydrocarbons and thus to provide economical initial materials for a number of chemical products.

Because of the high activity of the catalysts according to the invention and because of the isothermal mode of operation according to the invention, it is not necessary to load the catalysts thermally high. The mild reaction conditions produced from it lead not only to low operating and investment costs but also have an influence on the formation of by-products, by side reactions being substantially suppressed.

We claim:

1. A catalyst comprising chromium and aluminum oxides, at least one cesium metal compound promoter in an amount of 0.1 to 10% by weight of the catalyst, calculated as $Cs_2O$, and at least one zirconium metal compound as an additional promoter in a amount of 0.1 to 15% by weight of the catalyst, calculated as $ZrO_2$.

2. A catalyst according to claim 1, comprising an $Al_2O_3$ support with 10 to 50% by weight of chromium oxide, calculated as $Cr_2O_3$; 0.1 to 5% by weight of a zirconium compound, calculated as $ZrO_2$; and 0.1 to 10% by weight of a cesium compound, calculated as $Cs_2O$.

3. A catalyst according to claim 2, containing 0.5 to 1.5% by weight of said zirconium compound and 1 to 5% by weight of said cesium compound.

4. A catalyst consisting essentially of chromium and aluminum oxides, at least one cesium metal compound promoter in an amount of 0.1 to 10% by weight of the catalyst, calculated as $Cs_2O$, and at least one zirconium metal compound as an additional promoter in a amount of 0.1 to 15% by weight of the catalyst, calculated as $ZrO_2$.

5. A process for the dehydrogenation or dehydrocyclization of hydrocarbons on a regenerable catalyst comprising: contacting said hydrocarbons with said regenerable catalyst under sufficient dehydrogenation or dehydrocyclization conditions, wherein said regenerable catalyst comprises a chromium oxide and an aluminum oxide with at least one catalyst promoting cesium metal compound in an amount of 0.1 to 10% by weight of the catalyst, calculated as $Cs_2O$, and at least one additional promoter comprising at least one zirconium metal compound in an amount of 0.1 to 15% by weight of the catalyst, calculated as $ZrO_2$.

6. A process according to claim 5, wherein said catalyst comprises an $Al_2O_3$ support with 10 to 50% by weight of chromium oxide, calculated as $Cr_2O_3$; 0.1 to 5% by weight of a zirconium compound, calculated as $ZrO_2$; and 0.1 to 10% by weight of a cesium compound, calculated as $Cs_2O$.

7. A process according to claim 5, wherein the catalyst is an undiluted catalyst.

8. A process according to claim 5, wherein the hydrocarbons are contacted with the regenerable catalyst at a temperature between 400+ and 700° C. and under substantially isothermal conditions.

9. A process according to claim 5, wherein the hydrocarbons are contacted with the regenerable catalyst cyclically and during each cycle the temperature is raised.

10. A process according to claim 5, wherein the hydrocarbons are contacted with the regenerable catalyst at a pressure between 1 and 5 bars.

11. A process according to claim 5, wherein the hydrocarbons are fed at an hourly space velocity of 100 to 2,000 normal liters of hydrocarbon per liter of catalyst per hour.

12. A process according to claim 5, wherein the hydrocarbons are $C_3$, $C_4$ or $C_5$ hydrocarbon cuts or mixtures thereof, and said hydrocarbons are dehydrogenated to produce monoolefins.

13. A process according to claim 5, wherein the hydrocarbons are $C_6$ to $C_{10}$ hydrocarbon cuts, and said hydrocarbons are dehydrocyclized to produce benzene, toluene, and xylene aromatic compounds.

14. The process according to claim 12, further comprising feeding the monoolefins to a polymerization process and polymerizing them without interposition of a selective hydrogenation.

15. A process according to claim 5, further comprising regenerating the catalyst by contacting it with air having 2 to 20% by volume of $O_2$.

16. A process according to claim 15, wherein the catalyst is regenerated every 1 to 50 hours.

17. A process according to claim 5, wherein said regenerable catalyst contains 0.5 to 1.5% by weight of said zirconium metal compound, and 1 to 5% by weight of said cesium metal compound.

18. A process according to claim 5, wherein the regenerable catalyst consists essentially of said chromium oxide and aluminum oxide with at least one catalyst promoting cesium metal compound in an amount of 0.1 to 10% by weight of the catalyst, calculated as $Cs_2O$, and at least one additional promoter comprising at least one zirconium metal compound in an amount of 0.1 to 15% by weight of the catalyst, calculated as $ZrO_2$.

* * * * *

UNITED STATES PATENT AND TRADEMARK OFFICE
CERTIFICATE OF CORRECTION

PATENT NO. : 5,378,350
DATED : Jan. 3, 1995
INVENTOR(S) : Heinz ZIMMERMANN et al.

It is certified that error appears in the above-indentified patent and that said Letters Patent is hereby corrected as shown below:

Title page; item [73], Under Assignee: Insert the second assignee as follows:

Engelhard De Meern B.V.
        De Meern, Netherlands

Signed and Sealed this

Twenty-third Day of April, 1996

Attest:

BRUCE LEHMAN

*Attesting Officer*     *Commissioner of Patents and Trademarks*